United States Patent [19]

Singh

[11] Patent Number: 5,913,418

[45] Date of Patent: Jun. 22, 1999

[54] PACKAGED DENTAL FLOSS WITH MANUAL PRESSURE DISPENSING

[76] Inventor: Pritpal Singh, 5323 Port Sailwood Dr., Newark, Calif. 94560

[21] Appl. No.: 08/886,617

[22] Filed: Jul. 1, 1997

[51] Int. Cl.[6] .............................. A61B 19/02; A61C 15/04
[52] U.S. Cl. ........................ 206/63.5; 132/324; 206/388
[58] Field of Search .................................. 206/63.3, 63.5, 206/388, 581; 132/323, 324

[56] References Cited

U.S. PATENT DOCUMENTS

| | | |
|---|---|---|
| D. 289,973 | 5/1987 | Corella . |
| D. 295,020 | 4/1988 | Franchi . |
| 4,384,649 | 5/1983 | Brodsky . |
| 4,579,221 | 4/1986 | Corella ................................ 206/388 X |
| 4,643,305 | 2/1987 | De Roure Olivier .................... 206/388 |
| 4,693,365 | 9/1987 | Corella . |
| 5,110,007 | 5/1992 | Law et al. . |
| 5,263,585 | 11/1993 | Lawhon et al. .......................... 206/388 |
| 5,322,077 | 6/1994 | Corella . |
| 5,407,071 | 4/1995 | Lawhon et al. .......................... 206/388 |
| 5,549,201 | 8/1996 | Braude .................................... 206/388 |

*Primary Examiner*—Bryon P. Gehman
*Attorney, Agent, or Firm*—Chester Cekala

[57] ABSTRACT

A packaged dental floss is provided that includes a predetermined length of dental floss, suitable for a single use to floss a user's teeth, sealed within a cavity having walls of predetermined height, by a sealing film that is constructed to be ruptured by the user to dispense the floss from the cavity.

15 Claims, 3 Drawing Sheets

PACKAGED DENTAL FLOSS WITH MANUAL PRESSURE DISPENSING

BACKGROUND OF THE INVENTION

Tooth decay and dental disease can be caused by bacterial action resulting from the formation of plaque about the teeth and/or the entrapment of food particles in interstices between the teeth. Removal of plaque and entrapped food particles reduces the incidence of caries, gingivitis, and mouth odors as well as generally improving oral hygiene. Conventional brushing has been found to be inadequate for removing all entrapped food particles and plaque.

To supplement brushing, dental flosses and tapes have been recommended. Many dental flosses are formed of a plurality of long, continuous filaments. Other dental flosses are formed of a gel (referred to herein as "gel flosses"), such as those described in co-pending application U.S. Ser. No. 08/699,891, filed Aug. 15, 1996.

Dental floss is typically packaged by winding many yards of the dental floss onto a small spool, placing the spool in a plastic housing having a hinged cover and a cutting blade, and allowing the free end of the floss to extend upward from the spool to a position in which it can be grasped by a user when the user opens the hinged cover. To dispense a length of floss, the free end of the floss is grasped, a desired length of floss is pulled off of the spool, and the floss is cut by drawing it across the cutting blade.

SUMMARY OF THE INVENTION

The present invention features a packaged dental floss that does not utilize the conventional spool/housing/cutter arrangement. Instead, a predetermined length of dental floss, preferably a suitable length for a single use, is provided in a sealed single-use package. As a result, the user does not need to estimate the length of floss needed for flossing, does not need to cut the floss, and can carry several small, single-use packages when the user wishes to floss away from home, e.g., when travelling.

In one aspect, the invention features a packaged dental floss that includes a predetermined length of dental floss, suitable for a single use to floss a user's teeth, sealed within a cavity having walls of predetermined height, by a sealing film that is constructed to be ruptured by the user to dispense the floss from the cavity.

A packaged dental floss is provided having a sheet material defining a cavity, a length of dental floss in the cavity and a backing sheet sealing the floss in the cavity.

The term "blister pack" as used herein refers to a package that includes a rupturable sealing film, e.g., of plastic, paper or aluminum foil, and a semi-flexible "bubble" or "blister", generally of plastic, preferably transparent plastic, the backing sheet and blister being joined to form a sealed cavity in which the length of dental floss rests.

Other features and advantages of the invention will be apparent from the description of preferred embodiments thereof, taken together with the drawings, and from the claims.

DESCRIPTION OF THE PREFERRED EMBODIMENTS

Figure 1:
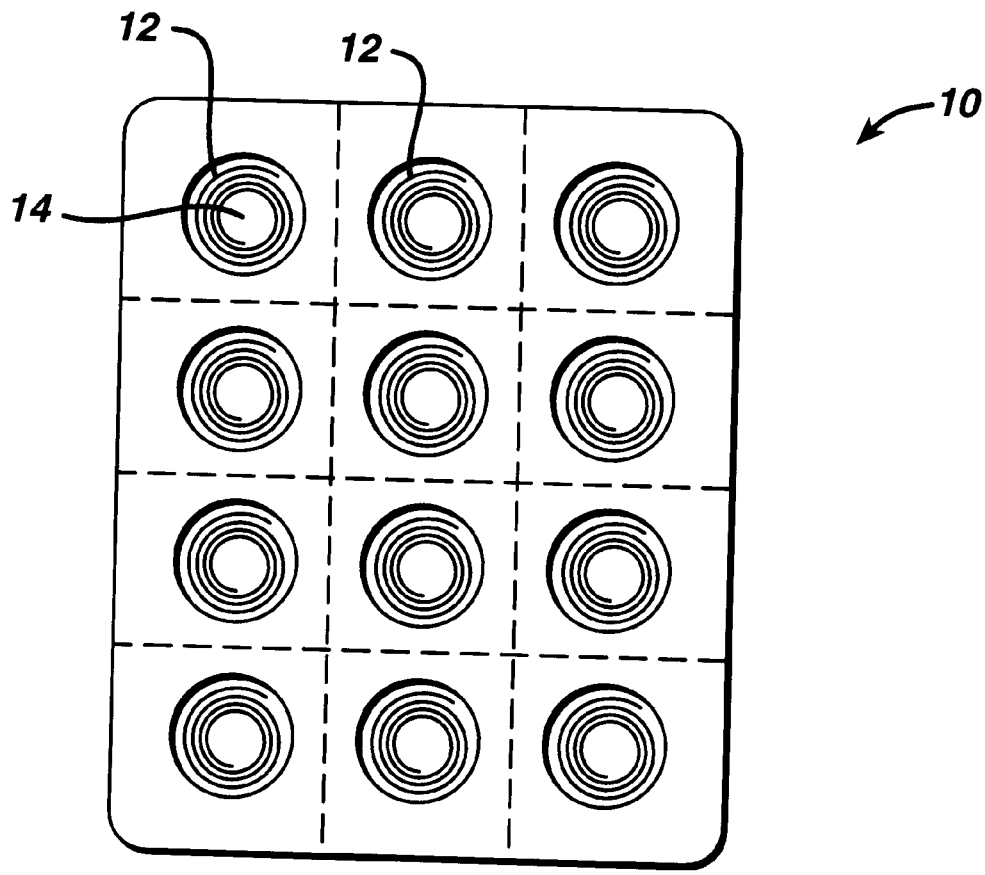
FIG. 1 is a top view of a packaged dental floss according to one aspect of the invention.
Figure 1A:
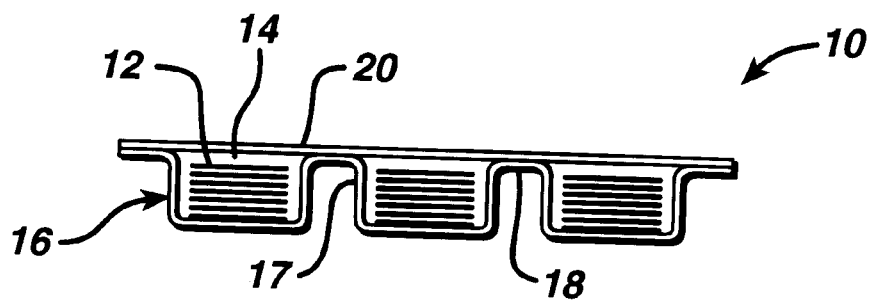
FIG. 1a is a side view of the packaged dental floss of FIG. 1.

As shown in FIGS. 1 and 1a, packaged dental floss 10 includes a plurality of coiled lengths of dental floss 12, each individual length of floss being sealed within a cavity 14 that is defined by a blister 16. Each individual length of floss has the same predetermined length as every other length of floss, and this predetermined length is selected to be suitable for a single use flossing a user's teeth. While floss 10 can be any desired type of dental floss or tape, gel floss is particularly well suited to use in the package of the invention.

Each blister 16 is formed in an otherwise planar top sheet 18 of, e.g., thermoformable plastic sheet material. A preferred material is a semi-rigid transparent plastic, e.g., cast vinyl. Blisters 16 may be formed by thermoforming a region of a planar plastic material to a desired shape, e.g., by placing the plastic material between a pair of male and female dies that are temperature controlled at a temperature sufficient to soften the plastic and pressing the male and female dies together to form an indentation or "blister" in the plastic. This technique is well known in the packaging art.

Preferably, the blister is round. This shape allows flosses, to drop into the blister in an orderly coil when the blisters are being filled during manufacturing. It is also preferred that the diameter of the blister 16 be selected to allow the floss to form an orderly coil, i.e., a coil in which substantially all of the loops are stacked. It is generally convenient for packing that the diameter be from about 5 to 30 mm. If the diameter is too large, the. floss may tend to form a randomly oriented pile that may be difficult for the user to unwind, while if the diameter is too small the floss may tend not to form a coil at all, or a desired length may not fit into the blister. The predetermined height of the side walls 17 of blister 16 may also affect coil formation, and is preferably selected to facilitate formation of an orderly coil, e.g., typical heights are typically from about 2 to 20 mm. If the blister 16 is too deep, the floss may tend to catch on the walls during filling of the blister, while if it is too shallow the desired length of floss may not fit into the blister.

To enclose the floss 12 within cavity 14, a sealing film 20 is joined to the top sheet 18. This sealing may be accomplished by heat, adhesives, or other suitable techniques. Preferably, the top sheet 18 is applied in a manner to form an air-tight and water-tight seal. The film 20 comprises a material to allow the floss 12 be pushed through film 20 when sufficient manual pressure is applied to blister 16.

Four alternative methods for inserting the floss into the blister are shown in FIGS. 2–5.

Figure 2:
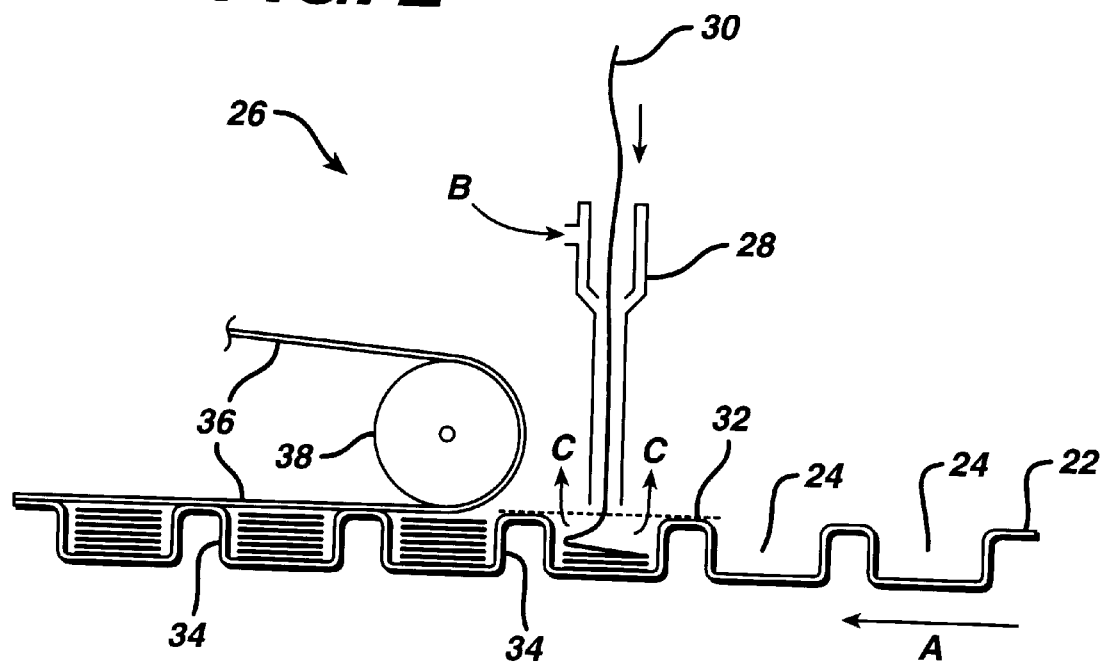
FIGS. 2–5 are schematic side views of processes for manufacturing a packaged dental floss according to alternative embodiments of the invention.

As shown in FIG. 2, a blister card 22, comprising a plurality of empty, open blisters 24 enters the production line 26 from the right, moving in the direction of arrow A. An air venturi or air nozzle 28 is positioned above the open blister card, and a continuous strand of floss 30 is threaded through air nozzle 28. Compressed air, typically 5–100 psi is then injected into the nozzle (see arrow B). As the air flows into the nozzle from the top and flows out at the other end, the air drags the strand of floss and forces the floss through the opening at the bottom of the air nozzle. Because the nozzle is positioned directly above an open blister 24, the floss is then propelled from the nozzle into the blister 24. During this process, the blister directly below the nozzle is covered with a wire mesh 32. Wire mesh 32 allows the strand 30 to enter through a hole in the mesh, but subsequently prevents the strand 30 from being blown or bounced from the blister. The mesh also allows air to escape from the blister as it is being displaced by the floss (arrows C). The blister card 22 is then moved to the left (arrow A) a sufficient distance to position the next empty blister 24 under the air nozzle, and the filled blister 34 is then covered by a sealing film 36, which passes from a spool (not shown) around a roller 38 and onto the blister card 22. The strand may then be cut by any suitable means to create a free end to start the next strand of floss.

Figure 3:
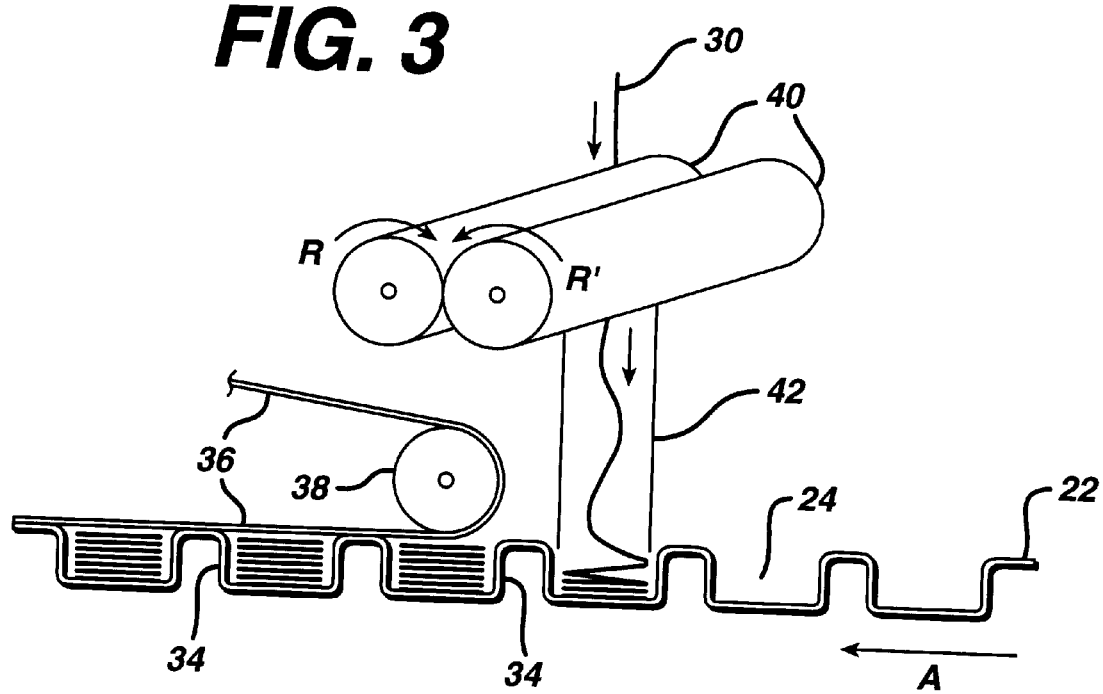

An alternative process is shown in FIG. 3. This process is similar to that described above, except that air nozzle 28 is replaced by a pair of rotating rollers 40. Rotating rollers 40 rotate in opposite directions (arrows R, R'), and thus act as pinch roller feeders, drawing the floss strand 30 downward. Either one or both of the rollers can be driven. A channel 42, having a diameter slightly smaller than that of the blister, runs from the blister up to the rollers, to contain the floss as it is fed toward the blister. Optionally, a wire mesh (not shown) similar to that shown in FIG. 2, or other suitable means for containing the floss strand within the blister prior to application of the sealing film 36 may be used.

Figure 4:
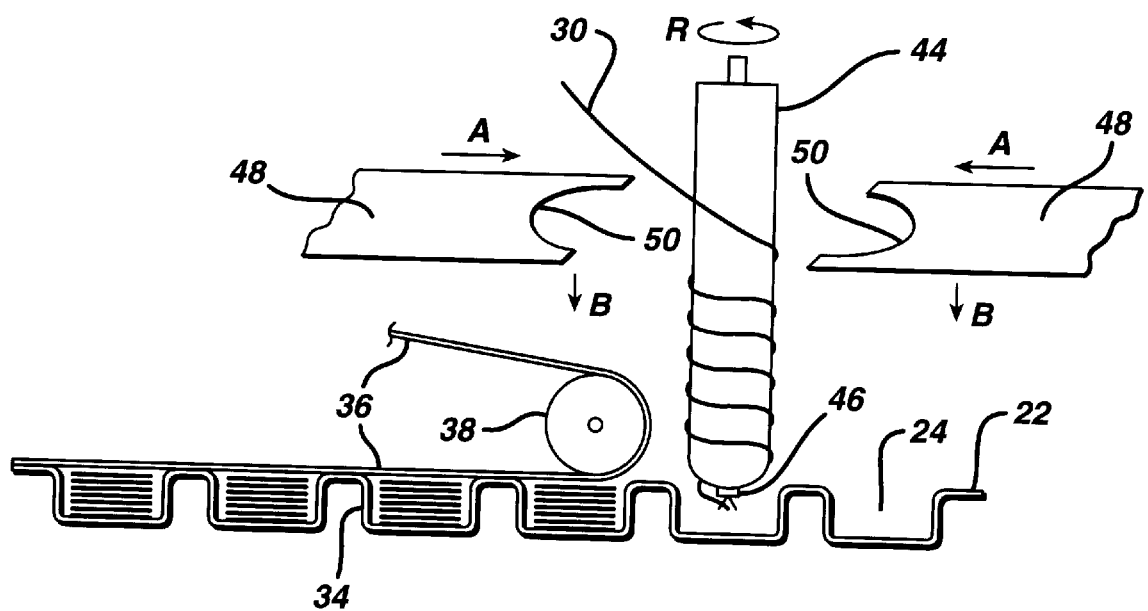

Another suitable manufacturing process is shown in FIG. 4. In the process shown in FIG. 4 the air nozzle and rotating rollers described above are replaced by a rotating cylinder 44, rotating in the direction indicated by arrow R. Preferably, cylinder 44 has a diameter slightly smaller than the diameter or width of the blister, and has a non-stick surface, e.g., a surface that is TEFLON® polymer coated, or highly polished to prevent sticking of gel flosses and minimize frictional resistance. It is also preferred that cylinder 44 be long enough to hold a desired length of floss 30 in a coil on the cylinder. An empty blister 24 is positioned under the cylinder 44, and the free end of floss 30 is gripped by a gripping/cutting/release mechanism 46 at the bottom of the cylinder. The cylinder is then rotated for a predetermined number of rotations, to coil the floss around the cylinder as shown in FIG. 4. When a desired number of coils is on the cylinder, side plates 48 are moved towards each other (arrows A) so that their arcuate surfaces 50 form a ring around the outer surface of cylinder 44, either with a small clearance or lightly contacting the cylinder. The side plates are then moved downwards (arrows B), sliding the coils of floss 30 down the cylinder and into blister 24. The gripping/cutting/release mechanism 46 will then release the free end of the floss and cut the floss at a desired position at the top of the coil.

Figure 5:
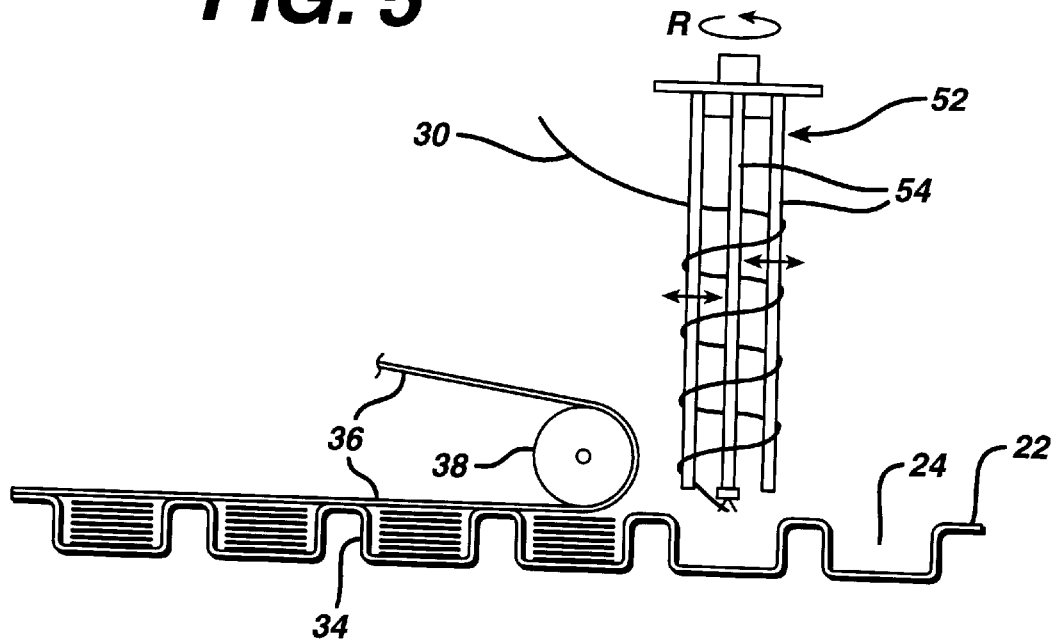

FIG. 5 shows another alternative packaging process. This process again is similar to those described above, but in this process the floss 30 is fed downward by a rotating collapsible cylinder 52, made up of a plurality of radially moveable rods 54. The collapsible cylinder 52 coils the floss 30 in the same manner as the rotating cylinder 44 described above. The coils are then moved downward into the blister by collapsing the cylinder (i.e., by moving the rods inward towards the longitudinal axis of the cylinder), allowing the coils to slip off the cylinder, rather than pushing them downward with side plates 48.

While preferred embodiments are disclosed, other modifications and alterations may be made by those of ordinary skill without departing from the spirit and scope of the invention.

For example, while several alternative manufacturing processes have been described above, other processes capable of inserting the floss into a cavity in a substantially coiled form, and sealing the cavity, may be used.

What is claimed is:

1. A packaged dental floss comprising:
   a sheet material defining a cavity having a predetermined height;
   a length of dental floss disposed in said cavity; and
   a backing sheet sealingly disposed with respect to said cavity to cover said cavity and retain the length of dental floss therein, wherein said backing sheet comprises a material constructed to deflect in response to manual pressure applied to said cavity to allow said length of dental floss to be pushed through said backing sheet when sufficient manual pressure is applied to an outer surface of said cavity.

2. The packaged dental floss of claim 1 wherein said sheet material comprises transparent plastic.

3. The packaged dental floss of claim 1 wherein said length of dental floss is coiled.

4. The packaged dental floss of claim 1 wherein said dental floss comprises a gel floss.

5. The packaged dental floss of claim 1 wherein said backing sheet is sealed to said sheet material around the periphery of said cavity to form a water-tight and air-tight seal.

6. A packaged dental floss according to claim 1 wherein said backing sheet comprises a film that is manually rupturable by the user to dispense the floss from the cavity.

7. The packaged dental floss of claim 6 wherein said cavity is round.

8. The packaged dental floss of claim 6 wherein said cavity has a predetermined diameter that is selected to allow the floss to form an orderly coil as it is being inserted into the cavity during manufacturing.

9. The packaged dental floss of claim 6 wherein said cavity has a diameter of from about 5 to 30 mm.

10. The packaged dental floss of claim 6 wherein said cavity has a predetermined height that is selected to allow the floss to form an orderly coil as it is being inserted into the cavity during manufacturing.

11. The packaged dental floss of claim 6 wherein said cavity has a height of from about 5 to 20 mm.

12. The packaged dental floss of claim 6 wherein the dental floss is a gel floss.

13. A packaged dental floss product comprising:
   a sheet material defining a plurality of spaced cavities;
   a plurality of lengths of dental floss, one said length of dental floss being disposed in each of said cavities; and
   a backing sheet sealingly joined to said sheet material to cover said cavities, wherein said backing sheet comprises a material constructed to deflect in response to manual pressure applied to applied to a respective said cavity to allow a respective said length of dental floss to be pushed through said backing sheet when sufficient manual pressure is applied to an outer surface of said cavity;
   said sheet material and said backing sheet having regions defined by perforated borders between said cavities to enable said sheet material and backing sheet to be torn into sections containing a number of said cavities designated by a user of said packaged dental floss product.

14. A method of dispensing a length of dental floss provided within a sealed package comprising a cavity in a sheet material that is constructed to deflect in response to manual pressure applied to said cavity and a backing sheet sealed to the sheet material to cover the cavity that is constructed to allow the length of dental floss to be pushed through said backing sheet when sufficient manual pressure is applied to an outer surface of said cavity;
   comprising the step of applying sufficient manual pressure to an outer surface of said cavity to push said length of dental floss through said backing sheet.

15. A method of packaging a dental floss into a plurality of unconnected portions of dental floss, each portion having a predetermined length suitable for a single use to floss a user's teeth, comprising steps of inserting each of said portions, respectively, into a different cavity having walls of predetermined height and sealing said cavities with a sealing film that is manually rupturable by the user to push the floss through the sealing film when sufficient manual pressure is applied to an outer surface of one of said cavities to dispense the floss from said one cavity.

* * * * *